United States Patent [19]
Eckert et al.

[11] Patent Number: 4,946,385
[45] Date of Patent: Aug. 7, 1990

[54] CASE FOR DISPENSING ORTHODONTIC ELASTIC RINGS

[75] Inventors: Robert P. Eckert, Alta Loma; Benjamin A. Shabtay, Arcadia, both of Calif.

[73] Assignee: Unitek Corporation, Monrovia, Calif.

[21] Appl. No.: 296,417

[22] Filed: Jan. 5, 1989

Related U.S. Application Data

[63] Continuation of Ser. No. 132,922, Dec. 15, 1987, abandoned.

[51] Int. Cl.⁵ .................................................. A61C 3/00
[52] U.S. Cl. .......................................... 433/2; 433/18; 221/310; 206/63.5; 206/805
[58] Field of Search ................. 433/2, 3, 4, 13, 15, 433/18, 22, 229; 206/63.3, 63.5, 303, 445, 805, 820, 822; 221/310, 312 C

[56] References Cited

U.S. PATENT DOCUMENTS

| | | | |
|---|---|---|---|
| 1,414,946 | 5/1922 | Graham | 221/310 |
| 2,481,495 | 9/1949 | Borthwick | 221/310 |
| 3,231,976 | 2/1966 | Wallshein | 433/3 |
| 3,530,583 | 9/1970 | Klein et al. | 433/18 |
| 3,758,947 | 9/1973 | Kesling | 433/18 |
| 4,026,021 | 5/1977 | Kesling | 433/2 |
| 4,038,753 | 8/1977 | Klein | 433/18 |
| 4,071,948 | 2/1978 | Deutzmann | 221/310 |
| 4,217,686 | 8/1980 | Dragan | 29/413 |
| 4,436,510 | 3/1984 | Klein | 433/4 |

Primary Examiner—John J. Wilson
Attorney, Agent, or Firm—Donald M. Sell; Walter N. Kirn; James D. Christoff

[57] ABSTRACT

A case for holding and dispensing small components such as orthodontic O-rings. Most of the component is fictionally or otherwise retained within the case, and only a small component portion extends from the case to be accessible to and grasped by the tips of a plier-like extraction tool. The case prevents the tool tips from closing over the entire component which would require component repositioning before placement.

8 Claims, 3 Drawing Sheets

U.S. Patent   Aug. 7, 1990   Sheet 1 of 3   4,946,385
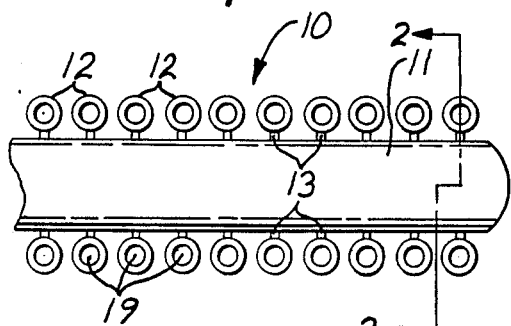
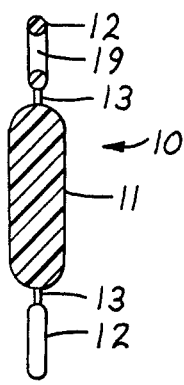
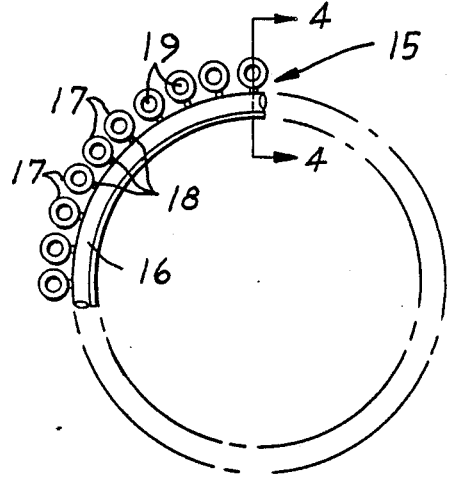
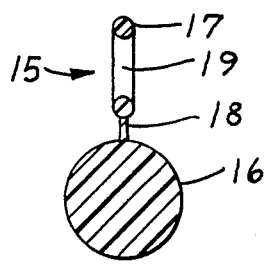
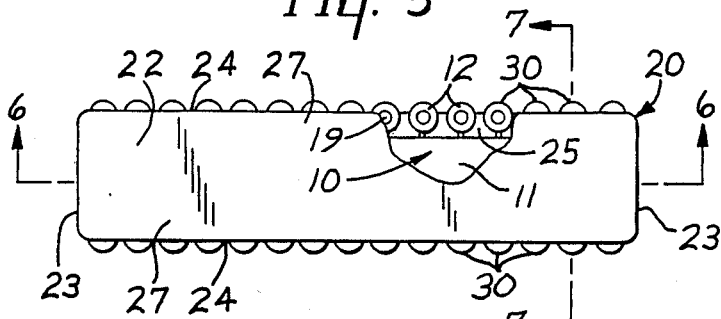
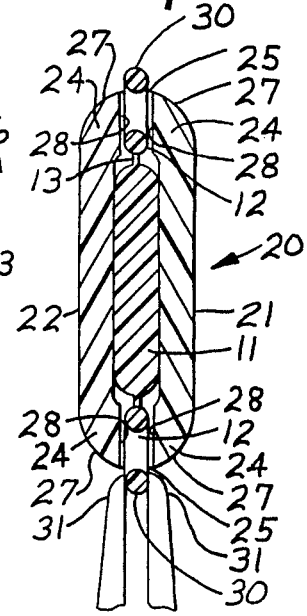
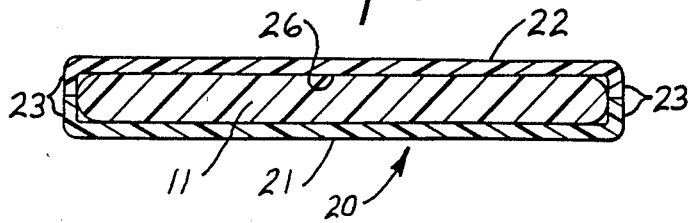

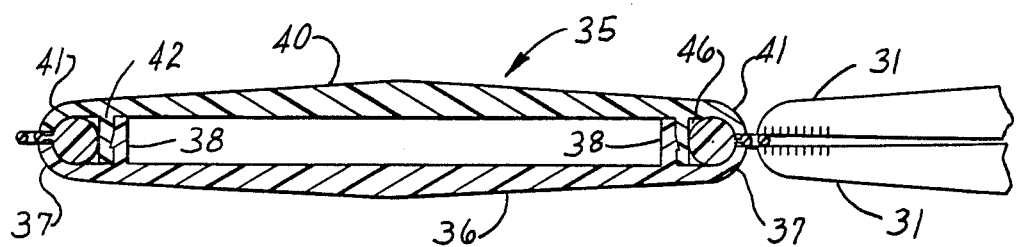
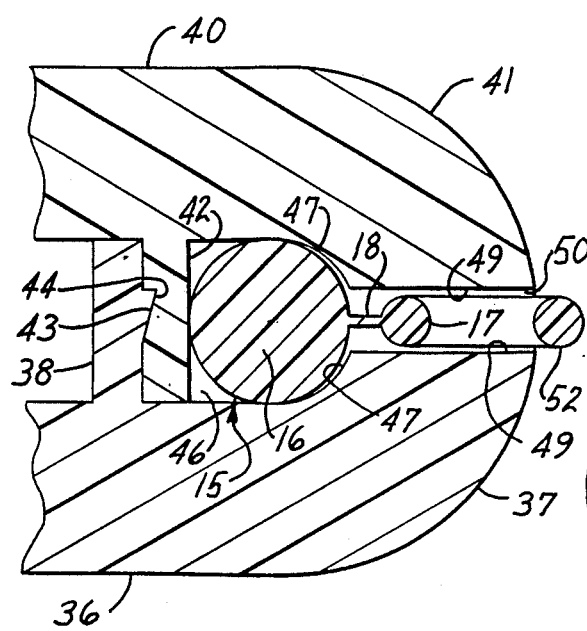
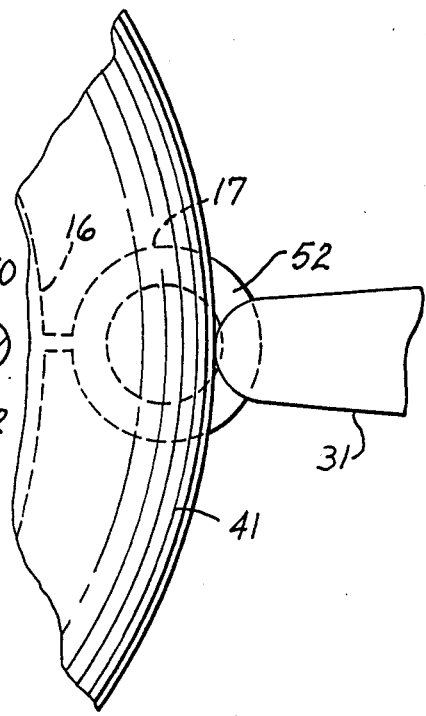

CASE FOR DISPENSING ORTHODONTIC ELASTIC RINGS

This is a continuation of application Ser. No. 07/132,922 filed 12/15/87, abandoned.

BACKGROUND OF THE INVENTION

Elastic O-rings are in widespread use as orthodontic devices for ligating an arch wire to an orthodontic bracket, and for applying corrective forces to teeth. These elastomeric rings are described in detail in U.S. Pat. No. 3,530,583 and U.S. Pat. No. 3,758,947, and they are typically made of a plastic material which is resistant to mouth fluids and able to maintain long-duration elasticity in the mouth environment. The rings are usually of toroidal or donut shape, but may be oval or otherwise configured, and the term O-ring is used herein to include all such shapes.

In common with almost all intraoral orthodontic appliances, the elastic rings are quite small, and in a typical size for ligation have an outside diameter of one-eighth inch or less, and an inside diameter of less than one-sixteenth inch. When first commercially introduced, these rings were supplied loose in bulk containers, and the orthodontist or assistant was forced to pick up an individual ring with the fingers or a forcep for alignment and subsequent placement in the mouth. This proved inconvenient, and rings were often dropped, or unwanted multiple rings might inadvertently be withdrawn from the bulk container.

This handling problem was partially solved by the development of an integrally molded assembly of many rings each joined by a frangible branch or neck to a central core which was conveniently handheld. An individual ring is gripped by a plier or forcep, and snapped off the core for realignment between the tips of the gripping tool and placement in the mouth. Various configurations of such as are disclosed in U.S. Pat. No. 4,038,753 and U.S. Pat. No. 4,217,686.

The molded assembly or O-ring "tree" is popular with orthodontists, but the problem remains of realigning the now-separated O-ring between the gripping-tool tips so the tips do not cover or obscure the ring central opening (the "hole in the donut"). This opening must remain clear so the ring can be installed (e.g., stretched and fitted over the tie wings of an orthodontic bracket when the ring is used to ligate an arch wire in place), and the tiny ring must be painstakingly repositioned between the tool tips or beaks to achieve the desired alignment.

This invention eliminates the time-consuming repositioning step by housing the O-rings in a case or dispenser which prevents the grasping-tool tips from passing over the ring central hole by exposing for gripping only a small annular portion of the ring. The tool tips are stopped by the dispenser in a fashion which prevents the tips from obscuring the ring opening, and the resulting automatic ring alignment eliminates the annoying repositioning procedure.

SUMMARY OF THE INVENTION

The invention relates to a case for retaining and partially enclosing small components such as orthodontic O-rings which must be held with a substantially open and unobscured central opening during placement on an orthodontic appliance. The O-rings are indexed in predetermined positions in a case channel or groove, and only a small outer portion of each ring extends from the case for contact with a gripping tool used to remove the O-ring from the case. Case sidewalls overhanging the channel or groove prevent intrusion of the gripping tool over the O-ring central opening, thereby positioning the O-ring for immediate placement on an intraoral appliance.

BRIEF DESCRIPTION OF THE DRAWINGS

FIG. 1 is a plan view of an integrally molded O-ring tree;

FIG. 2 is a stepped and enlarged sectional view on line 2—2 of FIG. 1;

FIG. 3 is a plan view of an integrally molded ring-shaped core carrying a number of O-rings;

FIG. 4 is a sectional view on line 4—4 of FIG. 3;

FIG. 5 is a plan view, partially broken away, of a case for housing and dispensing O-rings of the tree style shown in FIGS. 1 and 2;

FIG. 6 is a sectional side view on line 6—6 of FIG. 5;

FIG. 7 is an enlarged sectional end view on line 7—7 of FIG. 5;

FIG. 8 is a sectional side view of another dispensing case for use with O-rings of the style shown in FIGS. 3 and 4;

FIG. 9 is an enlarged sectional side elevation of a portion of the periphery of the case shown in FIG. 9;

FIG. 10 is a plan view of the peripheral portion shown in FIG. 9;

DESCRIPTION OF THE PREFERRED EMBODIMENTS

Figure 11:
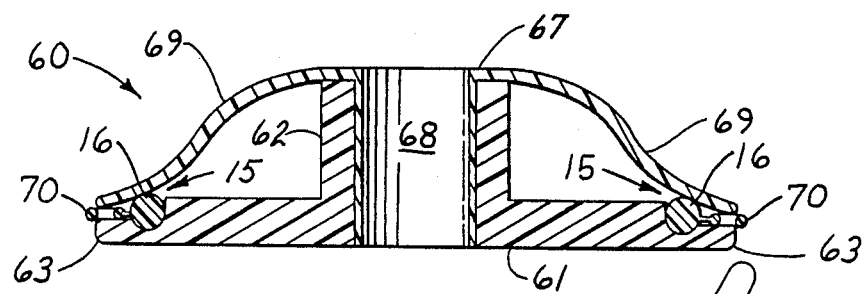
FIG. 11 is a sectional side elevation of a third embodiment of a dispensing case.

FIGS. 1 and 2 show a typical prior-art integrally molded O-ring assembly 10 having a central bar-shaped core 11 with a number of longitudinally spaced-apart O-rings 12 extending from opposite sides of the core, each ring being joined to the core by a slender frangible neck 13. FIGS. 3 and 4 show another version which is an integrally molded O-ring assembly 15 with a continuous circular or ring-shaped core 16 having O-rings 17 extending radially outwardly from and joined to the core by frangible necks 18. These assemblies are described in greater detail in U.S. Pat. No. 4,038,753 and U.S. Pat. No. 4,217,686.

The assembly core is usually handheld by the orthodontist or assistant who uses a plier-like forcep with tips or beaks which grasp an individual O-ring and tear the ring from the core by stretching and breaking the frangible neck. As mentioned above, however, the O-rings are quite small, and the forcep tips are usually closed over the entire O-ring, thereby obscuring a central opening 19 of the O-ring, and requiring repositioning of the O-ring within the forcep tips so an intraoral appliance such as an orthodontic bracket can be fitted through the opening when the O-ring is elastically stretched over the appliance. FIGS. 5-7 show an orthodontic apparatus according to the present invention, comprises O-ring assembly 10 and an indexing case 20 made of two identical mating parts which are a base 21 and a cover 22. The base and cover have laterally extending end walls 23 which abut each other to be joined by sonic welding, an adhesive, integrally formed snaps, or any other convenient fastening means. The sides of the base and cover define shallow and laterally extending sidewalls 24 which terminate short of each other to define an open channel or slot 25 through each side of the case and extending into a hollow interior cavity or space 26 of the case. Outer surfaces 27 of the sidewalls are smoothly beveled or rounded as seen in FIG. 7.

Case interior space 26 is shaped and dimensioned to receive core 11 of O-ring assembly 10, with the core making a snug fit within the case interior. As shown in FIGS. 5 and 7, O-rings 12 extend within slots 25 when the case base and cover are secured together over the core. The width of slots 25 is chosen to provide either a slight clearance between facing ends 28 of the case sidewalls and the sides of the O-rings, or to place ends 28 in light frictional engagement with the O-ring side surfaces.

The case is dimensioned so each O-ring 12 has an outer portion 30 which extends from the case side beyond overhanging sidewalls 24, but the sidewalls substantially cover and obscure central opening 19 of the O-ring. In use, the beaks or tips 31 (FIG. 7) of a plier or conventional mosquito forcep are placed over and compressed against O-ring outer portion 30, and the ring is separated from the core by stretching the ring away from the core to break frangible neck 13. Sidewalls 24 prevent the forcep tips from entering case slot 25 over O-ring central opening 19, and this opening is accordingly unobscured by the tips after separation of the O-ring from the core. The separated ring is thus ready for immediate intraoral placement, and there is no need to reposition to O-ring within the forcep tips.

FIGS. 8–10 show another orthodontic apparatus according to the invention, which includes a case 35 and ring-shaped O-ring assembly 15. Case 35 includes a base 36 which is circular in planform, the base having a continuous and integrally formed annular sidewall 37 which curves upwardly from the base perimeter. A straight and upwardly extending continuous annular inner wall 38 is positioned radially inwardly of sidewall 37, and is integrally formed with the base.

Case 35 is completed by a cover 40 which is geometrically similar to base 36 and configured to mate with the base. Cover 40 is circular in planform, and has extending downwardly from its perimeter a curved sidewall 41. The cover also has a straight and downwardly extending continuous annular inner wall 42 positioned to fit snugly around inner wall 38 of the base. When the case is assembled, inner walls 38 and 42 may be adhesively joined or sonic welded, or may be provided with several projections 43 and mating sockets 44 (FIG. 9) for press-fitted snap-together assembly.

During assembly of the case halves, a ring-shaped O-ring assembly 15 is fitted in an annular cavity or space 46 defined between base 36 and cover 40 on the radially outer side of cover inner wall 42. Preferably, portions 47 of the inner surfaces of sidewalls 37 and 41 are smoothly curved to receive and fit against the radially outer surface of core 16 of the O-ring assembly. The core is preferably slightly compressed between portions 47 and the outer side of inner wall 42 to be fixed in position within the case.

As best seen in FIG. 9, sidewalls 37 and 41 have flat end surfaces 49 which are spaced apart slightly more than the cross-sectional diameter of O-rings 17 to define a continuous annular channel or slot 50 extending inwardly from the central perimeter of case 35 to annular space 46. Alternatively, end surfaces may lightly engage the side surfaces of O-rings 17, but should not make such a tight interference fit against the side surfaces that removal of the O-rings from slot 50 is impeded. In either case, the slot depth is selected to insure that central openings 19 of O-rings 17 are substantially covered and obscured by overhanging sidewalls 37 and 41. A very slight protrusion of the O-ring central opening from the case perimeter as suggested in FIG. 10 is acceptable, but 80 or 90 percent of the central-opening area should preferably be obscured.

In use, case 35 is conveniently held in the hand, and plier or forcep tips 31 are clamped over O-ring outer portion 52 which projects from the case perimeter (FIG. 10). The ring is then drawn away form the case and core 16 to rupture frangible neck 18, thereby freeing the O-ring from the case and core. As described above, O-ring central opening 19 is protected by overhanging sidewalls 37 and 41 against obscuration by the forcep tips, and the O-ring is properly positioned in the forcep for immediate intraoral placement.

Figure 12:
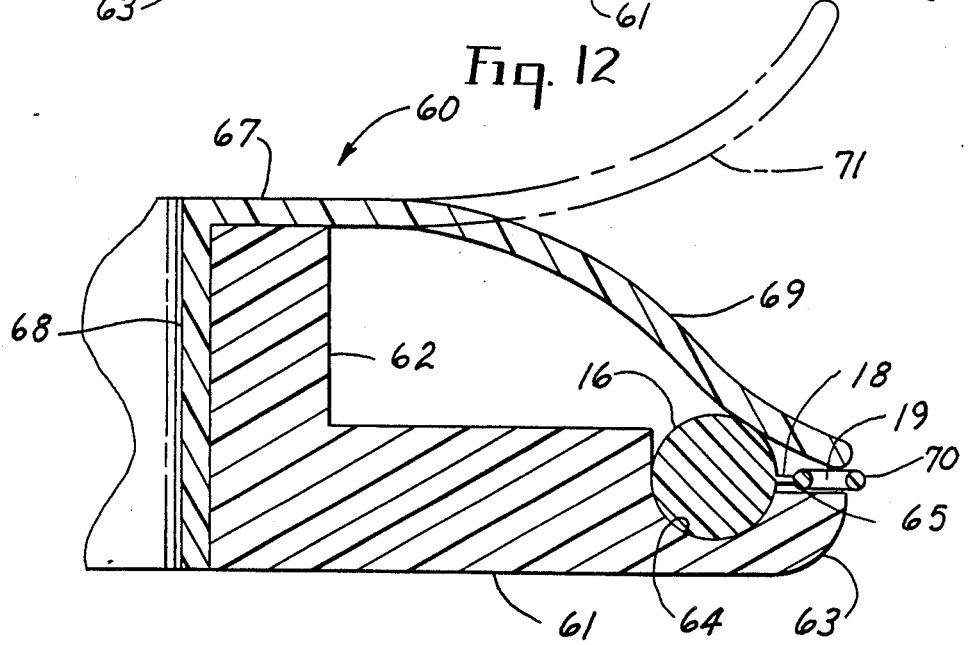
FIG. 12 is an enlarged sectional side elevation of a portion of the case shown in FIG. 11.

FIGS. 11 and 12 show another embodiment of the invention in the form of a case 60 having a solid circular-in-planform base 61 with a hollow upstanding central annular boss 62. The perimeter of the base defines a curved sidewall 63, and an annular recess 64 is positioned radially inwardly of a flat end surface 65 of the sidewall to receive core 16 of an O-ring assembly 15.

Case 60 has a cover member 67 with a tubular center section 68 secured within boss 62. A flexible skirt 69 extends radially outwardly from center section 68 to bear against and cover O-ring assembly 15 except for a protruding outer portion 70 of each O-ring 17. The O-ring central openings, however, are obscured by the perimeters of the base and cover, enabling outer portion 70 to be grasped by a forcep as described above, and with correct positioning in the forcep tips.

Flexible skirt 69 can be resiliently moved to an open position 71 shown in phantom line in FIG. 12 to enable reloading of the case with a fresh O-ring assembly. All of the cases described above, however, can be made of inexpensive plastic by conventional injection-molding methods, and will probably in most cases be treated as one-use products which are discarded when all O-rings have been stripped from the encased core.

Figure 13:
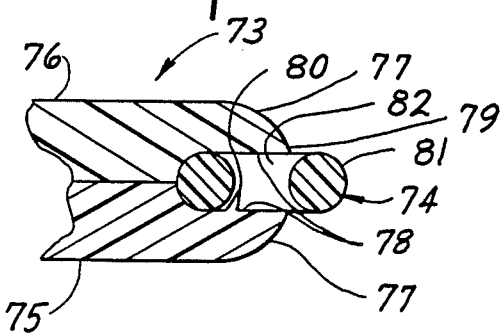
FIG. 13 is a sectional side elevation of a peripheral portion of a fourth style of dispensing case useful with loose O-rings.

It is not essential to the concept of the invention that the O-rings be integrally secured to a core in a multi-ring assembly, and machine loading of individual O-rings is also feasible. FIG. 13 shows the outer perimeter of a case 73 suitable for holding individual O-rings 74. Case 73 is of simple two-piece construction as described above, and includes a base 75 and·a cover 76 which when assembled define sidewalls 77 with facing flat inner surfaces 78 defining and overhanging an annular recess or slot 79 in the perimeter of the case.

Inner surfaces 78 of the sidewalls may be spaced apart slightly less than the cross-sectional diameter of O-rings 74 to provide frictional gripping retention of the O-rings, while still permitting forcep removal as described above. Alternatively, small and preferably flexible buttons or fingers 80 can be provided in the slot to retain the individual resilient rings until removed by forceps. In either case, only a small outer portion 81 of each O-ring extends from the case perimeter, and O-ring central openings 82 are thereby protected against forcep-tip obscuration when the O-ring is removed from the case.

The invention can be embodied in other case styles, and the invention objectives are met by any case which holds the O-rings until dispensing is desired, and which limits intrusion of the tweezer, plier or forcep tips to a small projecting portion of the O-ring to prevent the tips from extending across the O-ring central opening. The radial dimension of the projecting portion is preferably substantially equal to the cross-sectional diameter of the O-ring body, so the case walls overhang and shelter from the tool tips the O-ring central opening.

There has been described an O-ring dispensing case which holds O-rings in predetermined indexed positions with only a small radially outer portion of each ring being exposed for gripping during ring extraction. Automatic correct positioning of the O-ring in the extraction-tool tips is thereby provided, and the O-ring central opening remains substantially open and unobscured by the tips for immediate ring placement. The case has been described in the specific context of an orthodontic O-ring dispenser, but is equally useful in dispensing O-rings and similarly shaped small components where it is desirable to limit access of a grasping tool to only a small portion of the component.

What is claimed is:

1. Orthodontic apparatus comprising a case and a molded O-ring assembly having a core and plurality of spaced-apart O-rings each frangibly joined to the core, the O-rings having central openings, the case having a cavity receiving the core, the case having a pair of spaced-apart walls defining therebetween a slot in communication with the cavity and configured to receive the O-rings projecting from the core, the walls being configured to substantially cover the O-ring central openings while permitting respective portions of the rings to simultaneously extend beyond the walls and slot to be accessible to a gripping tool.

2. The apparatus defined in claim 1 wherein the walls are spaced apart a distance substantially corresponding to a cross-sectional dimension of the O-rings.

3. The apparatus defined in claim 1 wherein the cavity makes an interference fit with the O-ring assembly core to position and stabilize the core within the case.

4. The apparatus defined in claim 1 wherein the slot has a width smaller than the O-ring cross-sectional diameter so the O-ring makes an interference fit in the slot to be fictionally and releasably retained in the case.

5. The apparatus defined in claim 1 wherein one of the case walls is flexible so it can be resiliently moved away from the other wall to uncover the slot.

6. The apparatus of claim 1, wherein the core of the O-ring assembly is annular, and wherein the case is of generally circular mating shape, the slot extending around the perimeter of the case.

7. The apparatus of claim 1, wherein the core of the O-ring assembly is bar-shaped, wherein the case is generally rectangular in planform and has abutting end walls, the case having side edges defining the spaced-apart walls.

8. An O-ring dispenser for an elastomeric O-ring with a body of generally toroidal shape, the body having a generally circular central opening, comprising a case having spaced-apart walls defining therebetween a slot to receive the O-ring, the slot having a depth approximately equal to the outside diameter of the O-ring minus the cross-sectional dimension of the body, and the case being configured for releasably retaining the O-ring in the slot, whereby the O-ring has a body portion extending from the slot beyond the walls to be accessible for gripping by an extraction tool, and the walls prevent the tool from passing over and obscuring the central opening when the O-ring is in the slot, wherein the case defines a projection from one of the walls in the slot to extend within the central opening of an installed O-ring, whereby the projection retains the O-ring in the slot, and the O-ring can be removed from the slot by compressing the elastomeric body over the projection when the O-ring is extracted.

* * * * *